United States Patent
Springmann

[11] Patent Number: 5,873,252
[45] Date of Patent: Feb. 23, 1999

[54] CONDENSATE SEPARATOR

[75] Inventor: Thomas Springmann, Freilburg, Germany

[73] Assignee: Testo GmbH & Co., Lenzkirch, Germany

[21] Appl. No.: 904,714

[22] Filed: Aug. 1, 1997

[30] Foreign Application Priority Data

Aug. 1, 1996 [DE] Germany .................. 196 31 001.6

[51] Int. Cl.⁶ ................................... F25B 21/02
[52] U.S. Cl. .................................. 62/3.4; 62/3.7
[58] Field of Search ................... 62/3.2, 3.3, 3.4, 62/3.7, 404

[56] References Cited

U.S. PATENT DOCUMENTS

| | | | |
|---|---|---|---|
| 4,494,380 | 1/1985 | Cross | 62/3.2 |
| 4,506,510 | 3/1985 | Tircot | 62/3.4 |
| 4,593,529 | 6/1986 | Birochik . | |
| 5,361,587 | 11/1994 | Hoffman | 62/3.2 |
| 5,465,578 | 11/1995 | Barben et al. | 62/3.2 |
| 5,465,581 | 11/1995 | Haertl et al. | 62/50.1 |

FOREIGN PATENT DOCUMENTS

| | | |
|---|---|---|
| 2 528 321 A | 12/1983 | France . |
| 31 21 764 A1 | 12/1982 | Germany . |
| 35 41 645 A1 | 6/1987 | Germany . |
| 38 30 647 A1 | 3/1990 | Germany . |
| 39 37 017 A1 | 5/1991 | Germany . |
| 41 01 194 C1 | 8/1992 | Germany . |
| 42 29 177 C1 | 4/1994 | Germany . |
| 1 515 275 | 6/1978 | United Kingdom . |

*Primary Examiner*—William Doerrler
*Attorney, Agent, or Firm*—Foley, Hoag & Eliot LLP

[57] ABSTRACT

A condensate separator especially for a portable smoke or gas analyzer includes a condensate chamber (26) formed inside a housing (20) and sealed off from the environment. A gas supply element (30) is inserted into condensate chamber (26) and a gas discharge element (40) is provided to discharge gas from the condensate chamber (26). A Peltier element (10) having a hot side (12) and a cold side (14) is mounted on housing (20) and serves to cool the test gas flowing through condensate chamber (26), with cold side (14) being inserted almost completely into condensate chamber (26) so that it is in direct contact with the test gas. An elongated unheated test gas tube (100) supplies test gas to the condensate separator.

20 Claims, 1 Drawing Sheet

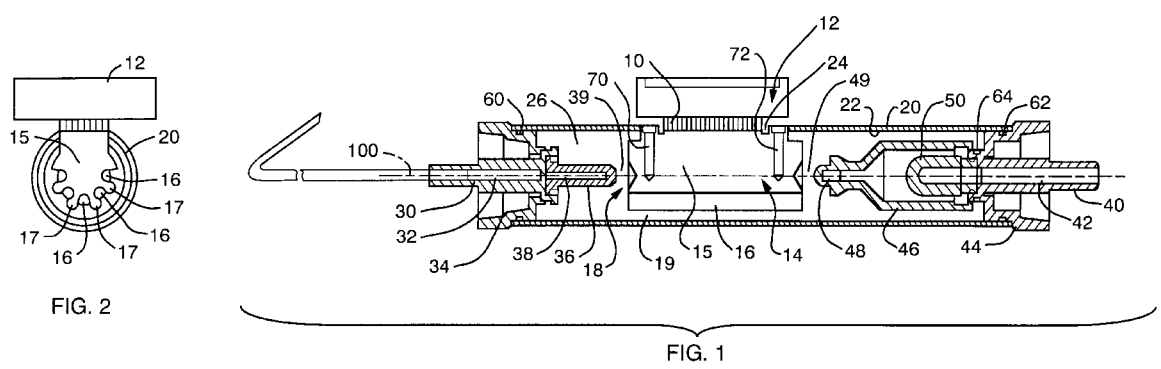

CONDENSATE SEPARATOR

BACKGROUND OF THE INVENTION

1. Field of the Invention

This invention relates to a condensate separator, especially for a portable smoke or gas analyzer, and more particularly relates to condensate separator for a gas analyzer having a Peltier element in the condensation chamber, which is in direct contact with the test gas to cool the test gas below the dew point thus causing condensation.

2. Description of the Related Art

To analyze flue gases from furnaces and exhaust from gas engines, a test gas is drawn in through a test gas probe and fed to an analyzer. To achieve adequate analysis results, it is important for the test gas to be properly prepared. This process typically involves removing moisture and dirt particles from the test gas.

The test gas is conducted by the probe through a test gas tube to the analyzer. If condensate from the test gas precipitates in the test gas tube, the test gas flowing through the test gas tube may contact the precipitated condensate for a relatively long period of time. Consequently, components of the test gas such as $NO_2$ and $SO_2$ may become trapped by the condensate, reducing the effective concentration of such components in the test gas, and thus leading to a distortion of the measured values of these components.

One known way to avoid occurrence of this source of measurement error is to heat the test gas tube and to provide a cooled condensate separator between the sampling probe and the analyzer. By heating the tube, it is possible to ensure that the test gas flowing therein will be maintained at or above the dew point temperature so that moisture will not condense in the test gas tube. Condensate separation then takes place exclusively and completely in a short space along the gas flow path, namely within the cooled condensate separator connected downstream from the test gas tube. The length of contact between the test gas and the liquid condensate is therefore limited to the vicinity of the condensate separator itself, so that only small quantities of $NO_2$ and $SO_2$ are trapped by the condensate. The concentrations of $NO_2$ and $SO_2$ in the test gas stream after passing through the condensate separator thus are practically the same as the concentrations in the flue gas to be analyzed. One example of a known condensate separator is shown in German Patent DE 42 29 177 C1.

Although the condensate separator described above has proven itself in principle, it suffers from a number of disadvantages. For example, problems occur when this apparatus is implemented in a mobile gas analyzer, designed for example for use by heating technicians or chimney sweeps, since a relatively large amount of energy is required to heat the test gas tube and to cool the gas in the condensate separator. These high energy requirements reduce the effective operating time of mobile gas analyzers, which are necessarily battery powered. Accordingly, frequent battery replacement is required.

The reasons for this comparatively poor efficiency are diverse in nature. In particular, the housing surrounding the condensate chamber must be cooled as a whole, and high energy is required for the cooling process because of the high thermal capacity of the housing. Moreover, high energy losses occur as a result of the loss of heat to the environment, which can be eliminated to only a very limited extent by insulation surrounding the housing. These and other problems limit the usefulness of certain known portable gas analyzers.

SUMMARY OF THE INVENTION

Accordingly, one object of this invention is to provide an improved smoke or gas analyzer which is energy efficient and which includes an energy efficient condensate separator. Another object of this invention is to provide a condensate separator which is energy efficient and which minimizes the absorption of test gas components by the condensate in the condensate separator so as to not distort measurement results. A further object is to provide a gas analyzer utilizing a relatively thin unheated elongated test gas tube to partially cool the test gas prior to reaching the condensate separator.

To achieve this and other objects, the condensate separator of this invention is provided with a condensate chamber through which the test gas flows, and which is provided inside a housing and sealed off from the environment. A Peltier element is mounted on the housing so that its cold side is thermally coupled to the housing. In this manner, the housing, and hence the inside wall facing the condensate chamber, is cooled to the point where the temperature prevailing in the condensate chamber, and hence the test gas temperature, can be lowered and kept below the dew point. Gas supply and removal elements are provided to convey the test gas to/from the condensate chamber.

The cold side of the Peltier element is located so that it is almost completely inside the condensate chamber, so that it is brought directly into contact with the test gas. The surface of the cold side of the Peltier element that serves as a heat exchanger is subjected to the direct flow of test gas, so that the heat exchange efficiency may be maximized. Further, thermal transmission losses are minimized since the cold source is applied directly where it is needed. In addition, the lowest temperature is inside the condensate separator, so that the temperature differential between the outside of the housing and the environment may be minimized.

According to one preferred embodiment, the cold side of the Peltier element is in thermal contact with the housing, specifically in the vicinity of any opening through which the Peltier element is passed. As a result, a portion of the cooling power is given off to the housing, so that the effective heat exchanger surface is considerably increased. Thus, condensate separation can take place not only on the cold side of the Peltier element itself but also on the inside wall of the housing. Although the temperature differential between the housing and the environment is increased by this measure, depending on the geometrical configuration, an improvement in overall efficiency can still be achieved since the condensate separator can be made smaller.

The improved efficiency of this condensate separator stems in part from the fact that the test gas flows around the cold source and therefore the outer surface to be insulated is smaller than in other configurations, in which a cold source is mounted externally and the test gas must flow through it. The outer surface to be insulated in the condensate separator according to the invention is therefore considerably reduced.

Another group of measures is aimed at optimizing heat transfer. Therefore, provision is preferably made to design the cold side of the Peltier element to be cylindrical. As the test gas flows over the element, the gas remains in contact over a relatively long distance with the cold source so that a decrease in test gas temperature below the dew point is maintained.

Another increase in the size of the cooling surface can be achieved in a simple fashion by additionally providing depressions, especially in the form of continuous axial grooves. By using a plurality of lengthwise grooves uniformly distributed around the circumference, an extremely effective yet compact increase in the heat transfer surface results.

Preferably, the cold side is brought close to the inside wall of the condensate chamber to form a radial gap, so that the continuous axial grooves form a plurality of gas-conducting paths that are largely separated from one another and communicate with one another only through the radial gap. Thus the test gas stream is thereby divided into a plurality of partial streams that are conducted along relatively narrow paths and provide effective and uniform cooling of the entire test gas stream.

An especially simple design for the condensate separator can be achieved if, according to a preferred embodiment, the housing consists of a cylindrical tube that is sealed at each end by plugs to form the condensate chamber. The plugs in turn support the gas-guiding elements, namely the supply element and the discharge element, which are preferably made integral with the respective plugs.

Preferably, each of the plugs supports a tap element, provided with bores, which projects into the condensate chamber. These elements produce a strong vorticization of the test gas streams due to the back flow zones that are produced. As a result, the zones additionally facilitate the condensing-out of droplets.

One of the two plugs, preferably the plug on the discharge side, supports a filter for separating particles. Fine particles made of polyethylene have proven especially satisfactory in this regard. They are connected in the path of the gas between the tap element and the gas-guiding element, with the location inside the tap element having the additional advantage that contact with the condensate is reliably prevented. One example of a suitable filter is disclosed, for example in connection with an uncooled condensate separator, in German patent No. 41 01 194 C1.

Further improvements are provided if the tap elements are located very close to the cold side that is designed as a heat exchanger element, forming an axial gap. This produces additional deflections and vorticizations that improve heat exchange.

In this connection it is optimal to design the end facing the tap element on the supply side as an impact surface for the test gas that emerges axially directly opposite the bore. The test gas emerges from the tap element at a high speed, and because of its high exit velocity, enters into intensive contact with the impact surface, so that a large part of the fluid can already be separated at this location.

When the measures described above are implemented, an extremely effective condensate separator can be provided which, because of its outstanding efficiency, can be small in size and can operate with a comparatively low cooling power. It is therefore especially suitable for use in gas analyzers which require low power consumption, such as portable gas analyzers.

A further reduction of cooling power and/or size can be achieved if, according to one preferred embodiment, the test gas tube connected to the gas supply element contributes to the cooling of the test gas, so that the test gas enters the condensate chamber already at a comparatively low temperature. A tube of this nature runs contrary to the prevailing view that the test gas must be heated on its way from the test gas probe to the condensate separator in order to prevent precipitation of condensate and the consequent distortion of the measured values, as mentioned at the outset. Thus, it has surprisingly been found that even without heating, condensate precipitation can be avoided by using an extremely small diameter, preferably in the range from 1.5 to 2.0 mm, to produce a flow rate in the test gas tube that is so high that, when combined with an optimum total tube length, preferably in the range from 2 to 4 m, the residence time of the test gas is so short that negligibly little if any absorption takes place during passage through the test gas tube. The use of such an unheated test gas tube for the type of measuring task usually encountered reduces the temperature to ambient temperature so that the required cooling power in the condensate separator can be further reduced. Use of a test tube of this nature is disclosed in a new U.S. patent application filed Aug. 1, 1997, by Thomas Springmann, entitled METHOD OF PREPARING A TEST GAS STREAM, Ser. No. (Attorney Ref No. FRM-00901), the contents of which are hereby incorporated by reference Since, apart from the reduced cooling requirement, no energy of any kind whatever is needed for the formerly conventional heating of the tube, the savings are enormous. This is evidenced especially positively in battery-operated analyzers, since their operating lives can be prolonged considerably without having to replace batteries.

Preferably, the test gas tube is made of Teflon since this material is sufficiently resistant to the aggressive components of the test gas. Moreover, this material has the property that droplets of condensate practically do not adhere to the surface and thus are entrained by the test gas stream. This prevents the condensate from remaining in the test gas tube in significant quantities. Other material exhibiting comparable properties may be used instead of Teflon. One criteria for selecting a suitable material is that the material should exhibit low absorption and adsorption for measurement-related components.

The configuration with the unheated test gas tube therefore consists of a two-stage gas cooler, with the first stage being formed by the test gas tube in which the test gas is cooled to ambient temperature. The second stage consists of the condensate chamber provided with the Peltier element, in which cooling to a temperature below the dew point, which is about 20° C. below the ambient temperature, takes place.

BRIEF DESCRIPTION OF THE DRAWING

The preferred embodiments of the present invention will now be described more specifically with reference to the attached drawings, in which FIG. 1 and FIG. 2 are partial cross-sectional views of a preferred embodiment of a condensate separator.

DETAILED DESCRIPTION OF THE PREFERRED EMBODIMENTS

The condensate separator has a housing in the shape of a tube 20 sealed at each end by plugs 34, 44 to form a condensate chamber 26. Sealing rings 60, 62 are provided between plugs 34, 44 and tube 20 to ensure a tight connection between these parts.

A tubular gas supply element 30 is molded integrally on plug 34, the element being traversed completely in the axial direction by a bore 32. A test gas tube 100 is mounted on gas supply element 30 and forms the connection to a sampling probe (not shown).

A tubular gas discharge element 40 is molded on plug 44, and is traversed completely in the axial direction by a bore 42. A line (not shown) extending to an analyzer can be attached to gas discharge element 40.

Tube 20 is provided with an opening 24 through which a Peltier element 10 is passed. Peltier element 10, in a known manner, is designed to have a hot side 12 and a cold side 14. The hot side 12 of Peltier element 10 is located outside tube 20 and serves to remove heat.

Cold side 14 of Peltier element 10 is located inside tube 20 and is therefore practically completely inside tube 20, and is specifically designed as a heat exchanger. For this purpose, cold side 14 has a cylindrical basic body 15 mounted on tube 20 by two screws 70, 72. A plurality of continuous grooves 16 running in the axial direction of Peltier element 10 are cut into basic body 15, with a ridge 17 remaining between each pair of adjacent grooves 16. The diameter of basic body 15 is dimensioned so that a radial gap 19 remains between ridges 17 and an inside wall 22 of tube 20.

Basic body 15, as a result of grooves 16, has a large surface for exchanging heat with the test gas flowing through the condensate separator. At the same time, individual gas-conducting paths are formed by grooves 16, the paths being essentially separated from one another and being linked with one another only by ridges 17 located therebetween in the vicinity of radial gap 19.

The basic body 15 and the tube 20 are in thermal contact in the vicinity of opening 24, so that tube 20 is also cooled to a certain degree. Thus, the inside wall 22 of the tube 20 is available as an additional heat exchange surface.

To improve the separation of condensate, flow deflection is also performed. For this purpose, plug 34 has a tap element 36 provided with an axial through bore 38, the element running concentrically to tube 20 and brought close to basic body 15 to form an axial gap 39. The test gas that emerges endwise from bore 38 through tap element 36 strikes basic body 15 endwise, with end 18 of the body thus acting as an impact surface. As a result of the impact, the test gas is initially deflected opposite to the impact direction before it is guided along basic body 15 following in another deflection.

A double deflection occurs downstream from basic body 15, due to the provision of an additional tap element 46 supported by plug 44. This element also has a bore 48 that runs coaxially with respect to tube 20. Tap element 46 is likewise brought close to basic body 15 to form an axial gap 49 so that the test gas stream can pass through this axial gap 49 and enter bore 48. Bore 48 terminates in the interior of tap element 46, which is sealed off from plug 44 by a sealing ring 64 and receives a filter 50 to separate particles. Thus, the empty interior of tube 20 is available as a condensate chamber 26. The filter 50 may be located in a portion of the tap element 46 which has a relatively large radial diameter to minimize the flow rate through the filter, and hence to minimize the pressure loss across the filter.

Unheated test gas tube 100 has an inside diameter of 3 mm and a length of 3 m. In the embodiment shown, test gas with a through flow volume of 0.9 l/min. is drawn off so that the residence time of the test gas in the test gas tube is less than 2 seconds. The residence time ensures that no measurement-relative absorption of $NO_2$ or $SO_2$ for example can take place. Teflon is used as the material for formation of the tube, to which condensate cannot adhere in significant amounts under the flow conditions described, but is entrained by the flow of test gas.

At a test gas temperature of approximately 180° to 250° C., in the vicinity of the test gas probe (not shown) a temperature of about 20° C. is achieved at the end of test gas line 100, i.e. in the vicinity of gas supply element 30. Thus, the test gas is cooled in the test gas tube 100 to ambient temperature.

In addition, during operation, the initial condition required for measurement (reducing the temperature in condensate chamber 26 to a value below the dew point) is achieved. Accordingly, measurement values can be obtained in a very short time.

The test gas tube 100 may thus be provided in an uninsulated state while still preventing absorption of $NO_2$ and $SO_2$, by increasing the throughput rate of the test gas to minimize its residence time in the test gas tube. Preferably, the flow rate is set to a value of at least 1.5 m/s. By increasing the throughput rate, it no longer becomes necessary to provide an insulating jacket around the test gas tube, thus enabling a thin walled gas tube to be utilized to minimize the weight of the gas analyzer.

Specifically, this effect may be achieved when the average flow rate of the test gas stream, in other words averaged over the flow cross section, assumes a value of at least 1.5 m/s. It currently appears that the best results are achieved when the flow rate is set to a value in the range from 4.0 m/s and 7.0 m/s. Increases of the flow rate above about 7 m/s do not appear advantageous, since further reduction of the absorption of $NO_2$ and $SO_2$ no longer significantly influences the measurement results, while the flow resistance increases sharply with the consequence that a delivery pump with an increased power draw is required.

The conditions mentioned above for the flow rate also ensure that drops of condensate that precipitate on the walls of the test gas tube 100 cannot adhere to the walls of the test gas tube 100, but are entrained by the stream of test gas and transported to the condensate chamber 26 of the condensate separator.

For most of the measurement tasks that occur in practice, the measurement error caused by the absorption of $NO_2$ and $SO_2$ can be reduced to negligible levels if the average residence time of the test gas stream in the test gas tube is less than 3 seconds. A measurement error of less than 1% can be achieved if, according to a preferred variation on the method, the residence time is in the range from 0.25 sec to 1.0 sec.

Special advantages are obtained by using a test gas tube made of Teflon. This material is sufficiently resistant to aggressive components of the test gas and also has a surface structure that makes it difficult for condensate droplets to adhere, so that these droplets are especially easily entrained by the test gas stream.

Preferably, a test gas tube with an inside diameter in the range from 1.5 mm to 4.0 mm is used. More preferably, the inside diameter should be set to approximately 2.0 mm. The above diameter figures are adjusted to the particular measurement tasks being undertaken in the field of exhaust technology and also to take into account the conventionally installed delivery capacity of the test gas pump that sucks the test gas stream out of the exhaust stream. This power permits a delivery volume of approximately 0.9 l/min. Taking into account the average data found for the state of the test gas as well as the flow resistances, the speed condition for the test gas stream described at the outset is obtained. A diameter of less than about 1.0 mm, under practical conditions, results in flow resistances that are so high that the installed pumping power is no longer sufficient. With an inside diameter of more than about 4.0 mm on the other hand, the flow rate in the test gas tube will already have been reduced to the point that significant measurement errors occur because of increased absorption of $NO_2$ and $SO_2$.

As far as the length of the test gas tube used is concerned, lengths been about 1.5 m and 5.0 m have proven advantageous. They can, of course, be varied if necessary to adjust the final temperature at the connection to the condensate separator. Usually a length of about 3 m is sufficient to ensure cooling to ambient temperature for conventional measuring tasks, depending on the thermal characteristics of the tube material and the geometric configuration of the tube.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art which this invention pertains.

This application claims priority from German Application No. 196 31 001.6-52, the content of which is hereby incorporated by reference.

What I claim is:

1. A condensate separator for use with a portable gas analyzer, comprising:
   a condensate chamber sealed off from the environment and disposed inside a housing capable of receiving a test gas;
   a gas supply for introducing the test gas into the condensate chamber;
   a gas discharge for discharging the test gas from the condensate chamber; and
   a Peltier element having a hot side and a cold side, said Peltier element being mounted on the housing such that the cold side of the Peltier element is inserted almost completely into the condensate chamber to cool the test gas in the condensate chamber and to directly contact the test gas in the condensate chamber, wherein the cold side of the Peltier element has a cylindrical shape with at least one of depressions and axial grooves formed on a surface thereof and wherein the cold side of the Peltier element is located close to an inside wall of the condensate chamber to form a radial gap so that a plurality of gas conducting paths are formed by the axial grooves and the inside wall of the condensate chamber.

2. The condensate separator according to claim 1, wherein the housing is in thermal contact with the cold side of the Peltier element in a vicinity of an opening through which the Peltier element passes.

3. The condensate separator according to claim 1, wherein the housing comprises a cylindrical tube sealed at one end by a supply plug and at another end by a discharge plug to form the condensate chamber, the supply plug being connected to the supply and the discharge plug being connected to the discharge.

4. The condensate separator according to claim 3, wherein the supply plug has a supply tap and the discharge plug has a discharge tap, each of said supply tap and discharge tap being provided with a bore extending axially through said tap to convey the test gas and each of said supply tap and discharge tap extending axially into the condensate chamber.

5. The condensate separator according to claim 4 wherein at least one of said supply plug and said discharge plug supports a filter connected in the gas path between the tap element and one of the supply and discharge.

6. The condensate separator according to claim 4 wherein each of said supply tap and said discharge tap are formed to closely approach the cold side of the Peltier element to form an axial gap.

7. The condensate separator according to claim 6 wherein a face of the cold side of the Peltier element facing the supply tap is designed as an impact surface for the test gas emerging axially from the bore in the supply tap.

8. The condensate separator according claim 7, wherein an unheated test gas tube having an inside diameter between 1.5 and 2.0 mm and a length between 2 and 4 m is connected to the gas supply element.

9. The condensate separator according to claim 8 wherein the test gas tube is made of Teflon.

10. A condensate separator for use with a portable gas analyzer, comprising:
    a condensate chamber sealed off from the environment and disposed inside a housing capable of receiving a test gas;
    a gas supply for introducing the test gas into the condensate chamber;
    a gas discharge for discharging the test gas from the condensate chamber;
    a Peltier element having a hot side and a cold side, said Peltier element being mounted on the housing such that the cold side of the Peltier element is inserted almost completely into the condensate chamber to cool the test gas in the condensate chamber and to directly contact the test gas in the condensate chamber; and
    an unheated elongated test gas tube for supplying test gas to the condensate separator is connected to the supply, said unheated elongated test gas tube having an inside diameter below 3 mm and a length between 2 and 4 m.

11. A condensate separator for use with a portable gas analyzer, comprising:
    a condensate chamber sealed off from the environment and disposed inside a housing capable of receiving a test gas;
    a gas supply for introducing the test gas into the condensate chamber;
    a gas discharge for discharging the test gas from the condensate chamber; and
    a Peltier element having a hot side and a cold side, said Peltier element being mounted on the housing such that the cold side of the Peltier element is inserted almost completely into the condensate chamber to cool the test gas in the condensate chamber and to directly contact the test gas in the condensate chamber, wherein the cold side of the Peltier element is located close to an inside wall of the condensate chamber to form a radial gap so that a plurality of gas conducting paths are formed by axial grooves on the surface of the cold side and the inside wall of the condensate chamber.

12. The condensate separator according to claim 11, wherein the housing is in thermal contact with the cold side of the Peltier element in a vicinity of an opening through which the Peltier element passes.

13. The condensate separator according to claim 11, wherein the cold side of the Peltier element has a cylindrical shape.

14. The condensate separator according to claim 11, wherein the housing comprises a cylindrical tube sealed at one end by a supply plug and at another end by a discharge plug to form the condensate chamber, the supply plug being connected to the supply and the discharge plug being connected to the discharge.

15. The condensate separator according to claim 14, wherein the supply plug has a supply tap and the discharge plug has a discharge tap, each of said supply tap and discharge tap being provided with a bore extending axially through said tap to convey the test gas and each of said supply tap and discharge tap extending axially into the condensate chamber.

16. The condensate separator according to claim 15 wherein at least one of said supply plug and said discharge plug supports a filter connected in the gas path between the tap element and one of the supply and discharge.

17. The condensate separator according to claim 15 wherein each of said supply tap and said discharge tap are formed to closely approach the cold side of the Peltier element to form an axial gap.

18. The condensate separator according to claim 17 wherein a face of the cold side of the Peltier element facing the supply tap is designed as an impact surface for the test gas emerging axially from the bore in the supply tap.

19. The condensate separator according claim 18 wherein an unheated test gas tube having an inside diameter between 1.5 and 2.0 mm and a length between 2 and 4 m is connected to the gas supply element.

20. The condensate separator according to claim 19 wherein the test gas tube is made of teflon.

* * * * *